(12) United States Patent
Schugt

(10) Patent No.: US 7,318,264 B2
(45) Date of Patent: Jan. 15, 2008

(54) MONOLITHIC INTEGRATED CIRCUIT/PRESSURE SENSOR ON PACING LEAD

(75) Inventor: Michael A. Schugt, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/675,961

(22) Filed: Feb. 16, 2007

(65) Prior Publication Data
US 2007/0151351 A1  Jul. 5, 2007

Related U.S. Application Data

(62) Division of application No. 11/096,150, filed on Mar. 31, 2005, now Pat. No. 7,231,829.

(51) Int. Cl.
G01L 7/10 (2006.01)

(52) U.S. Cl. .............. 29/25.42; 29/594; 29/595

(58) Field of Classification Search ........... 600/472; 29/25.42, 594, 595; 204/408, 424
See application file for complete search history.

(56) References Cited

U.S. PATENT DOCUMENTS

| | | | |
|---|---|---|---|
| 5,189,777 A | 3/1993 | Guckel et al. | |
| 5,353,800 A | 10/1994 | Pohndorf et al. | |
| 5,357,807 A | 10/1994 | Guckel et al. | |
| 5,564,434 A | 10/1996 | Halperin et al. | |
| 5,679,902 A | 10/1997 | Ryhanen | |
| 5,719,069 A | 2/1998 | Sparks | |
| 5,834,333 A | 11/1998 | Seefeldt et al. | |
| 6,012,336 A | 1/2000 | Eaton et al. | |
| 6,149,599 A * | 11/2000 | Schlesinger et al. | 600/472 |
| 6,171,253 B1 | 1/2001 | Bullister et al. | |
| 6,199,575 B1 | 3/2001 | Widner | |
| 6,203,523 B1 | 3/2001 | Haller et al. | |
| 6,221,024 B1 | 4/2001 | Miesel | |
| 7,231,829 B2 * | 6/2007 | Schugt | 73/729.2 |
| 2004/0073137 A1 | 4/2004 | Lloyd et al. | |
| 2004/0237285 A1 | 12/2004 | Rangsten et al. | |

\* cited by examiner

Primary Examiner—Jewel Thompson
(74) Attorney, Agent, or Firm—Daniel G. Chapik

(57) ABSTRACT

A pressure module is provided which comprises a capsule having a cavity formed therein, and a pressure transducer disposed within the cavity of the capsule. A feedthrough pin, fixedly coupled to the capsule, extends into the capsule and is electronically coupled to the pressure transducer.

10 Claims, 4 Drawing Sheets

MONOLITHIC INTEGRATED CIRCUIT/PRESSURE SENSOR ON PACING LEAD

CROSS REFERENCE TO RELATED APPLICATION

This application is a divisional application of U.S. Ser. No. 11/096,150, filed Mar. 31, 2005 now U.S. Pat. No. 7,231,829 entitled "Monolithic Integrated Circuit/Pressure Sensor on Pacing Lead."

FIELD OF THE INVENTION

The present invention generally relates to pacing leads, and more particularly relates to a pressure sensor module for incorporation into a pacing lead.

BACKGROUND OF THE INVENTION

Blood pressure monitoring may be used to assist a medical practitioner in diagnosing cardiovascular and other conditions of a patient. In many instances, blood pressure is monitored indirectly since this technique is relatively non-invasive and is useful for obtaining an approximate blood pressure measurement. Typically, a sleeve is placed around a patient's limb, and the patient's blood pressure is measured on a pressure gauge coupled to the sleeve. In some circumstances, however, a more accurate blood pressure measurement may be needed. In such case, direct blood pressure monitoring, utilizing a device that is surgically implanted into a patient's bloodstream, may be employed.

Some direct pressure monitoring device configurations include a capsule having a pressure transducer disposed therein. The capsule includes an opening that allows fluid to contact the pressure transducer directly. When the device is appropriately deployed within the patient (e.g. within the patient's blood vessel proximate the patient's heart or within a chamber of the patient's heart), blood that is pumped by the heart exerts pressure against the pressure transducer. The pressure transducer, in turn, senses the exerted pressure and communicates a signal representative of the sensed pressure to a pressure measurement gauge or other appropriate pressure measuring device.

Although the above-mentioned pressure monitoring devices are useful in many circumstances, they may have certain drawbacks. For example, because the pressure transducer directly contacts the patient's blood, it may be more susceptible to corrosion. Thus, in cases in which the pressure transducer includes an integrated circuit chip, the device may degrade over time. Furthermore, blood may coagulate around the capsule opening, which may, in turn, affect pressure transducer operation. As a result, these types of pressure monitoring devices may not be suitable for long-term pressure monitoring.

In recent years, pressure monitoring devices have been developed to overcome the aforementioned drawbacks by encasing a pressure transducer within a fluid-filled, smooth-surfaced capsule and rigidly attaching the pressure transducer to the capsule. The capsule includes a flexible diaphragm disposed over an opening. When pressure is exerted on the diaphragm, the pressure is transferred to the pressure transducer via the fluid. The pressure transducer communicates with an implantable medical device or other appropriate medical device via a pressure monitoring lead. This device configuration decreases the corrosion experienced by the pressure transducer, reduces blood coagulation on the capsule, and may be implanted into a patient for relatively long-periods of time. However, when the pressure monitoring device is disposed within a patient's heart chamber, heart contractions may cause force to be applied to the lead, and therefore directly to the rigidly attached pressure transducer. This undesirable strain may decrease the structural integrity of the pressure monitoring device over time.

Accordingly, it is desirable to have a relatively simple and inexpensive pressure monitoring device that has a corrosion-resistant configuration and is capable of being implanted into a patient for long periods of time. In addition, it is desirable to have a pressure monitoring device that is configured to reduce strain due to lead movement. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A pressure sensor module is provided which comprises a capsule having a cavity formed therein, and a pressure transducer disposed within the cavity of the capsule. A feedthrough pin, fixedly coupled to the capsule, extends into the capsule and is electrically coupled to the pressure transducer.

In another exemplary embodiment, a pressure sensor module is provided for use in a medical lead including a wire conductor. The module comprises a capsule having a cavity formed therein, a biocompatible media disposed within the cavity of the capsule, a pressure transducer disposed within the biocompatible media, and a feedthrough pin fixedly coupled to the capsule. The feedthrough pin has a first end configured to be coupled to the wire conductor of the medical lead and has a second end configured to be flexibly coupled to the pressure transducer.

In still another exemplary embodiment, a method for manufacturing a pressure sensor module is provided comprising flexibly mounting a transducer in a cavity of a capsule and bonding a conductor between the pressure transducer and a feedthrough pin that is fixedly coupled to the capsule.

BRIEF DESCRIPTION OF THE DRAWINGS

The present invention will hereinafter be described in conjunction with the following drawing figures, wherein like numerals denote like elements.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Figure 1:
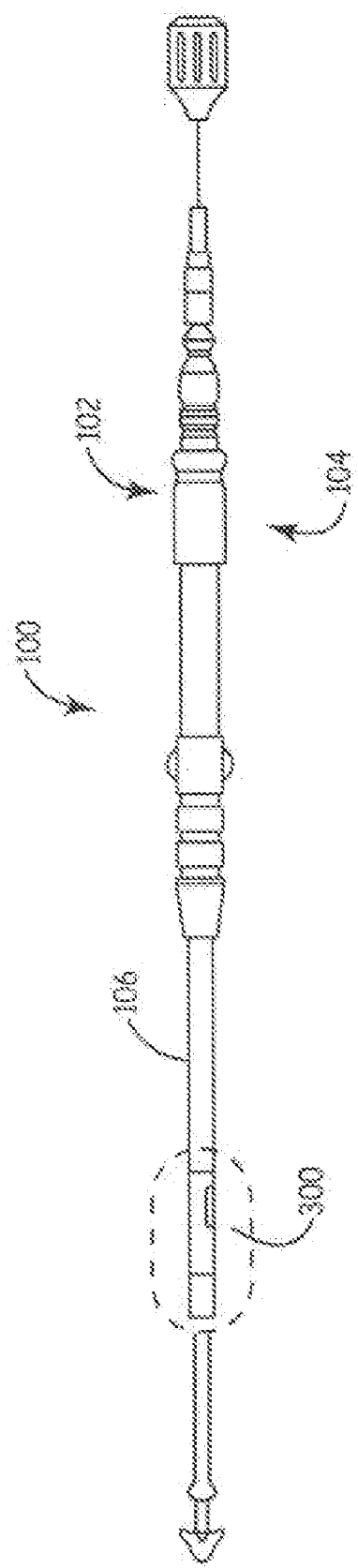
FIG. 1 is a side view of an exemplary lead.

FIG. 1 is a side view of an exemplary medical lead 100 configured to be coupled to an implantable medical device or other monitoring device (not shown) and includes a pressure sensor module 300. Lead 100 may be any one of a number of different types of leads; for example, a pressure monitoring lead, a therapy lead, etc. In any case, lead 100 includes a connector assembly 102, a lead body 106, and pressure sensor module 300. Connector assembly 102 is located at a proximal section 104 of lead 100 and may be configured to be coupled to an implantable medical device (not shown) to electrically couple lead 102 thereto.

Figure 2:
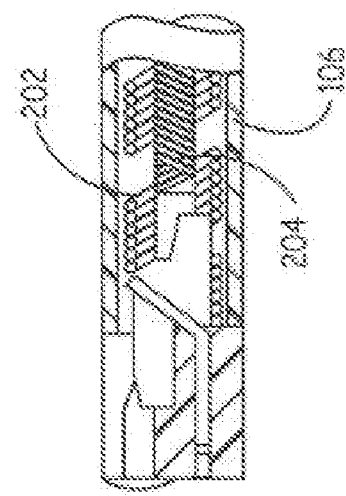
FIG. 2 is a cross sectional view of a portion of an exemplary lead body that may be implemented within the lead depicted in FIG. 1.

FIG. 2 is a cross-sectional view of an exemplary portion of lead body 106 including wire coils 202 and 204, each configured to electrically couple connector assembly 102 to pressure sensor module 300. Wire coils 202 and 204 are each depicted herein as single pole coiled wire conductors; however, it should be appreciated that any other suitable electrical configuration for coupling connector assembly 102 and pressure sensor module 300 may be employed. Furthermore, wire coils 202 and 204 may be made of any suitable biocompatible material such as titanium or the like.

Figure 3:
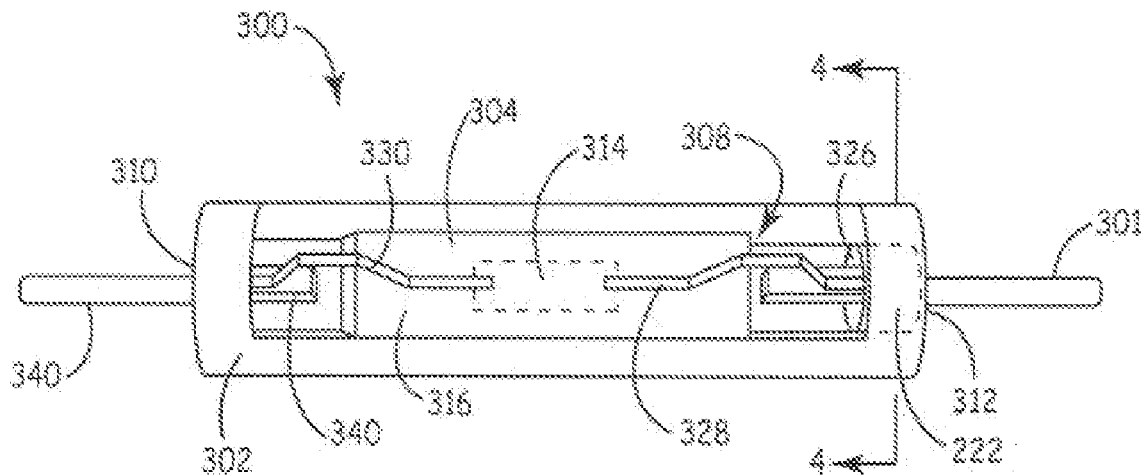
FIG. 3 is a top view of an exemplary pressure module that may be implemented within the lead depicted in FIG. 1 in accordance with a first embodiment of the present invention.
Figure 4:
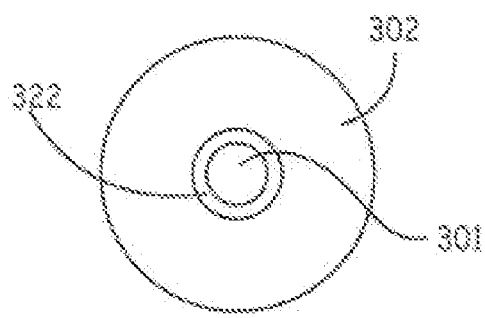
FIG. 4 is a cross sectional view of the lead depicted in FIG. 3 taken along line 4-4.

Referring to FIGS. 3 and 4, pressure sensor module 300 is configured to sense pressure exerted thereon by a patient's blood flowing therearound. Generally, pressure sensor module 300 includes a feedthrough pin 301, a capsule 302 having a cavity 308 therein, a pressure transducer 304, conductors 328 and 330 (e.g. a conductive ribbon), and an outer sheath 344 (shown in FIG. 5). As can be seen, feedthrough pin 301 extends into cavity 308, and pressure transducer 304 is positioned within cavity 308. Feedthrough pin 301 is insulated from capsule 302 by means of an insulative ferrule 322 (e.g. glass, plastic, etc.) that is provided through an end wall 312 of capsule 302. It should be noted that capsule 302, ferrule 322, and feedthrough pin 301 provide a rigid structure whether formed integrally or formed separately and subsequently assembled. A second feedthrough pin 340 may be provided through an opposite end wall 310 of capsule 302 in a similar manner. Wire conductor coils 202 and 204 (FIG. 2) may be electrically coupled to feedthrough pins 306 and 340. Capsule 302 may be formed of any suitable biocompatible material, such as titanium, or a biocompatible polymer. It should also be appreciated that while capsule 302 has been shown as an elongated tube, it may have any other suitable configuration.

Pressure transducer 304 includes an integrated circuit 314 on a substrate 316. Circuit 314 is configured to convert sensed pressure into representative electrical signals and may comprise a MEMS integrated circuit chip, discrete passive electrical components, etc. Circuit 314 is electrically coupled to feedthrough pins 301 and 340 by means of flexible conductors 328 and 330, respectively (e.g. titanium, niobium, or platinum wires or ribbons), using known bonding techniques; e.g. laser welding, wire bonding, etc. It should be noted that pressure transducer 304 is not coupled or attached to any other portion of capsule 302, and except for its attachment to conductors 328 and 330, pressure transducer 304 is effectively suspended within cavity 308.

Additionally, cavity 308 may be filled with a biocompatible substance, not shown, such as deionized watch, saline, silicone gel or the like, preferably a material that absorbs body electrolytes. If desired, pressure transducer 304 may be provided with a passivating layer (also not shown) for further protection. This passivating layer may comprise any one of a number of materials suitable for such purposes.

It should now be appreciated that due to the free-floating configuration of pressure transducer 304 within cavity 308, and the utilization of feedthrough pins 306 and 340 that are attached to capsule 302 by means described above, transducer 304 is provided with non-hermetic strain relief that is further enhanced through the use of a biocompatible material within cavity 308. That is, forces that are exerted on feedthrough pins 306 and 340 are transferred to capsule 302 and not to transducer 304. Furthermore, any motion imparted to conductors 328 and 330 due to such forces is cushioned or absorbed by the media contained within cavity 308 and surrounding transducer 304.

Feedthrough 306, as earlier suggested, electrically couples pressure transducer 304 to wire coil 202 to transmit a signal representative of pressure from integrated chip 314 to the non-illustrated implantable medical device. Feedthrough 306 is also configured to provide non-hermetic strain relief between pressure transducer 304 and lead 100 when module 300 is coupled to lead 100

Figure 5:
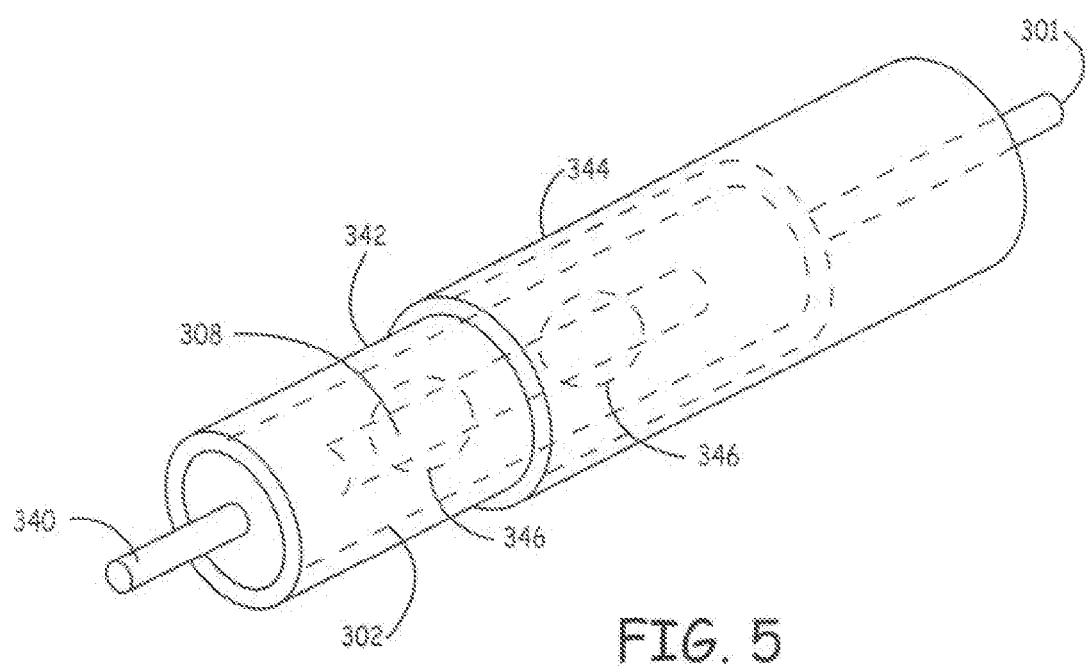
FIG. 5 is an isometric view the exemplary pressure module depicted in FIG. 3 having a sheath disposed therearound.

Referring to FIG. 5, capsule 302 may include an outer housing 342 and an outer sheath 344. Outer housing 342 is configured to house capsule 302 therein and includes one or more openings 346 therethrough that communicate with cavity 308. Outer housing 342 may be constructed of any one of a number of suitable materials as previously described. In one exemplary embodiment, outer sheath 344 is a sleeve that covers outer housing 342. In another exemplary embodiment, outer sheath 344 is a flexible diaphragm configured to be disposed over openings 346. In such case, outer sheath 344 is constructed of a biocompatible material that is flexible and responsive to pressure exerted thereon; for example, polyurethane or silicone. Biocompatible media is held within cavity 308 by outer housing 342 and outer sheath 344.

Figure 6:
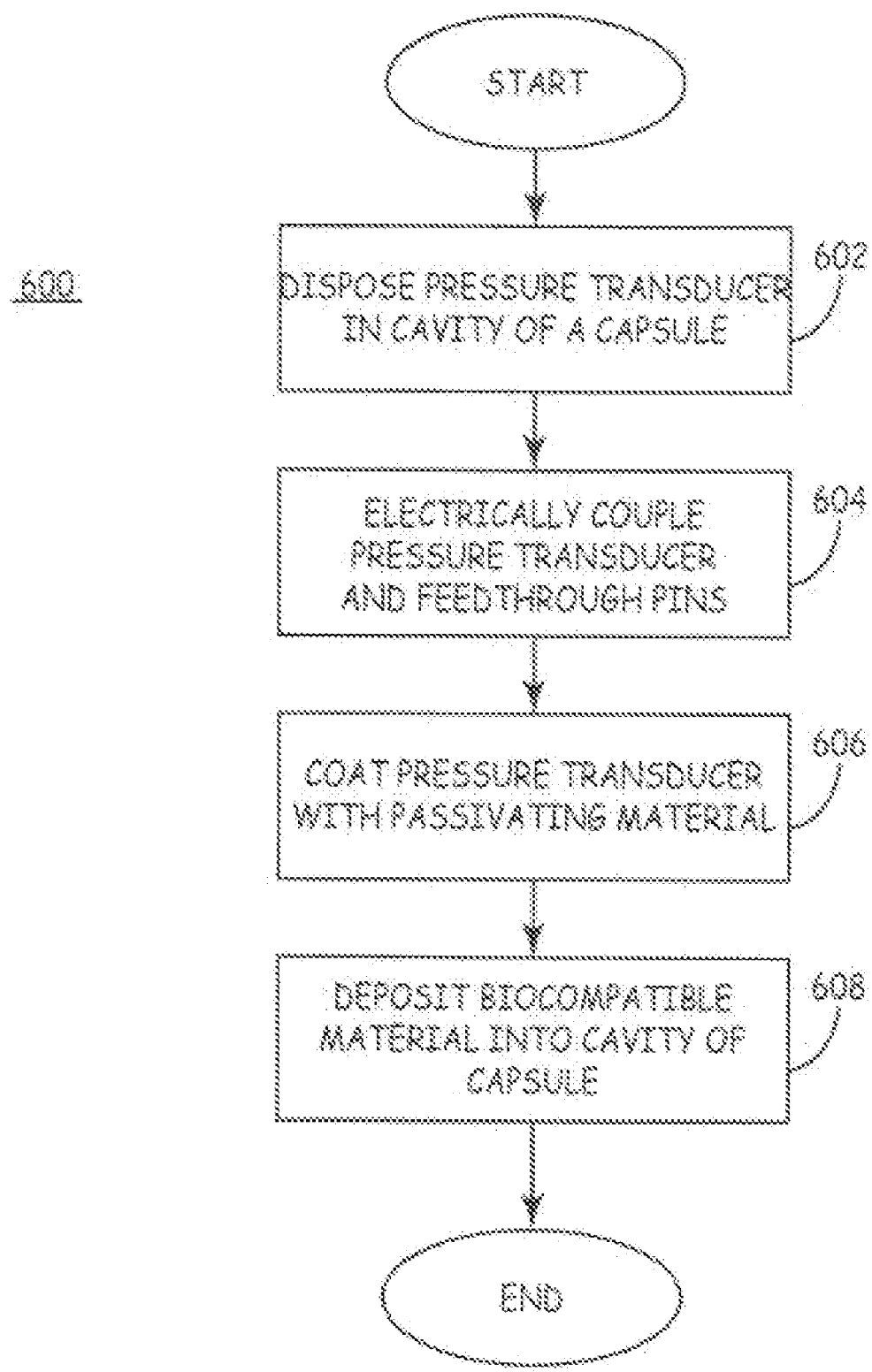
FIG. 6 is a flow chart illustrating an exemplary method for manufacturing the pressure capsule depicted in FIG. 3.

FIG. 6 is a flow diagram 600 of an exemplary method for manufacturing the above-described pressure sensor module 300. First, pressure transducer 304 is flexibly mounted in cavity 308 of capsule 302 (step 602). Next, transducer 304 and feedthrough pins 301 and 340 are electrically coupled to one another (step 604). Pressure transducer 304 may be coated with a passivating material to form a passivating layer (step 606), followed by depositing biocompatible material in cavity 308 (step 608).

With regard to step 602, pressure transducer 304 may be obtained from any one of numerous sources. For example, pressure transducer 304 may be manufactured to include conductors 328 and/or 330 pre-bonded thereto, or alternatively, without pre-bonded conductors. Alternatively, pressure transducer 304 may comprise a standard off-the-shelf item obtained from any one of numerous sources. Capsule 302 first may be machined from an appropriate material to include end openings, and appropriately configured insulative ferrules each having a passageway therethrough inserted into the end openings. Conductive pins are then inserted through the insulative ferrules. Capsule 302 is then heated to affix the conductive pins to the insulative ferrules. Alternatively, the feedthrough pins 301 and 340 may be integrally formed as part of capsule 302.

Pressure transducer 304 is flexibly mounted within cavity 308 by, for example, depositing biocompatible potting material to partially fill cavity 308, positioning pressure transducer 304 on the deposited potting material, and electrically coupling the pressure transducer to feedthrough pins 301 and 340 (step 604) by, for example, laser welding, wire bonding, soldering, parallel gap welding, and the like. If not already provided, a passivating layer may be deposited over pressure transducer 304 by, for example, the deposition of any suitable material (step 606). Finally, cavity 308 is substantially filled with biocompatible media (step 608). If biocompatible material is gel-like, it may be deposited directly into cavity 308 via a dispenser and may be heated, cooled, or the like, in order to set module components therein. If biocompatible media is more liquid, capsule 302 may be inserted into outer housing 342 and covered with outer sheath 344. If outer sheath 344 is a sleeve, outer housing 342 is inserted into outer sheath 344. If outer sheath 344 is a sheet of material, outer sheath 344 is placed over window 346 and coupled to outer housing 342. In either case, cavity 308 is sealed and biocompatible fluid may be introduced into cavity 308 via, for example, a fill port (not shown) that may be pre-machined into capsule 302.

Thus, apparatus and methods have been provided for a relatively simple and inexpensive pressure monitoring device that is has a corrosion-resistant configuration and is capable of being implanted into a patient long-term. In addition, the apparatus provides accurate blood pressure measurements.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

The invention claimed is:

1. A method for manufacturing a pressure sensor module comprising:
   flexibly mounting a transducer in a cavity of a capsule; and
   bonding a conductor between the pressure transducer and a feedthrough pin fixedly coupled to the capsule.

2. The method of claim 1, further comprising:
   depositing a biocompatible media into the cavity of the capsule.

3. The method of claim 2, wherein the step of mounting comprises positioning the pressure transducer in the biocompatible media.

4. The method of claim 1, wherein the step of mounting comprises:
   insulating said feedthrough pin from said capsule by means of an insulating ferrule through a wall of said capsule; and
   heating the insulative ferrule, feedthrough pin, and capsule to fixedly couple the feedthrough pin to the insulative ferrule and the insulative ferrule to the capsule.

5. The method of claim 1, further comprising:
   coating said pressure transducer with a passivating material.

6. The method of claim 1, further comprising:
   mounting said capsule in an outer housing, wherein said outer housing includes an opening therethrough.

7. The method of claim 6, further comprising:
   depositing fluid media between the capsule and said outer housing.

8. The method of claim 7, where in the step of mounting comprises positioning the capsule in the fluid media.

9. The method of claim 6, further comprising:
   mounting a resilient diaphragm over at least said opening.

10. The method of claim 7, wherein the step of mounting comprises positioning the capsule in the fluid media.

* * * * *